United States Patent [19]
Fujiwara et al.

[11] Patent Number: 4,767,870

[45] Date of Patent: Aug. 30, 1988

[54] METHOD OF PURIFYING L-ASCORBIC ACID

[75] Inventors: Yoshitaka Fujiwara; Tetsuji Kaizu, both of Yamaguchi, Japan

[73] Assignee: Takeda Chemical Industries, Ltd., Osaka, Japan

[21] Appl. No.: 880,820

[22] Filed: Jul. 1, 1986

[30] Foreign Application Priority Data

Jul. 5, 1985 [JP] Japan ................................. 60-148923

[51] Int. Cl.$^4$ ........................................... C07D 307/62
[52] U.S. Cl. ..................................................... 549/315
[58] Field of Search ........................................ 549/315

[56] References Cited

U.S. PATENT DOCUMENTS 2,179,977 11/1939 Elger ................................... 549/315
2,265,121 12/1941 Reichstein ........................... 549/315

FOREIGN PATENT DOCUMENTS 760575 11/1956 United Kingdom .

*Primary Examiner*—Norma S. Milestone
*Attorney, Agent, or Firm*—Wegner & Bretschneider

[57] ABSTRACT

A method of purifying L-ascorbic acid which comprises: subjecting an acidic aqueous solution of L-ascorbic acid which contains salts of an inorganic acid to electrodialysis to remove the salt therefrom.

The method is in particular useful for removing salts of an inorganic acid from an aqueous mixture of L-ascorbic acid and the inorganic salt resulting from the production of L-ascorbic acid in which diacetone-2-keto-L-gulonic acid or 2-keto-L-gulonic acid is heated in the presence of an inorganic acid, or an alkyl ester of 2-keto-L-gulonic acid is enolized and lactonized in the presence of a base.

6 Claims, 1 Drawing Sheet

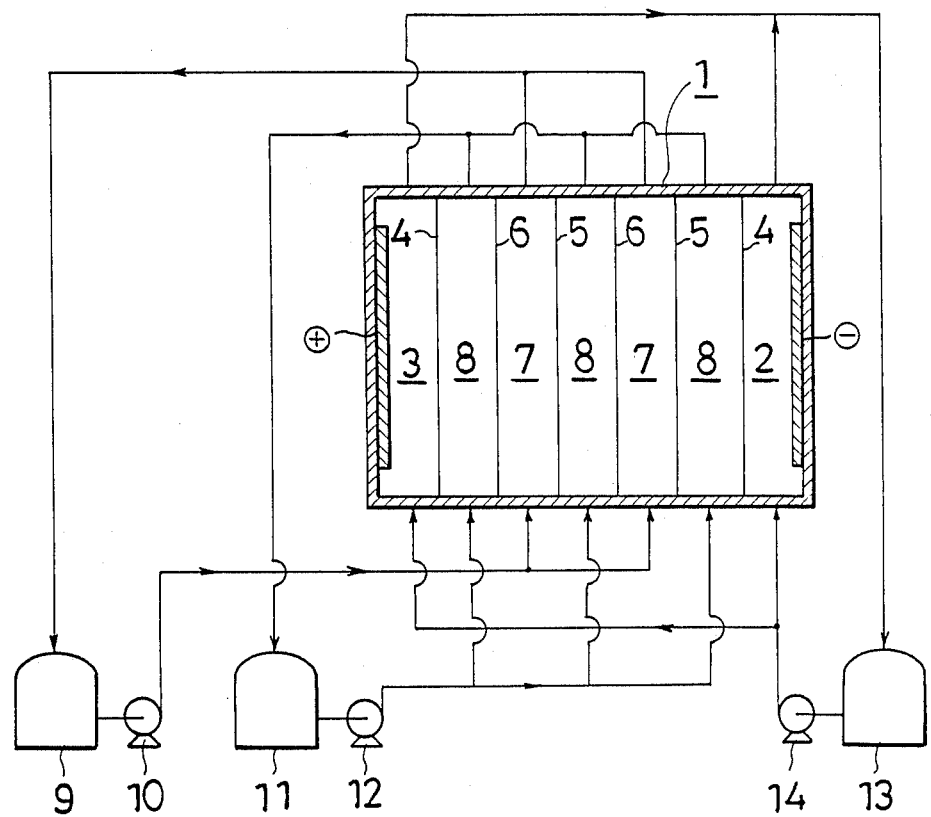

METHOD OF PURIFYING L-ASCORBIC ACID

This invention relates to a method of purifying L-ascorbic acid, and in particular, to a method of purifying L-ascorbic acid by removing therefrom salts of inorganic acids.

L-Ascorbic acid has been hitherto mainly produced by either of two processes. In one of the processes, diacetone-2-keto-L-gulonic acid or 2-keto-L-gulonic acid is directly enolized and lactonized in the presence of an inorganic acid to provide an aqueous mixture of L-ascorbic acid and the inorganic acid, as disclosed in U.S. Pat. No. 2,179,977, the process being hereinafter referred to as the direct process. In the other process, an alkyl ester of 2-keto-L-gulonic acid is enolized and lactonized in the presence of a base to provide an alkali metal salt or an alkaline earth metal salt of L-ascorbic acid, which is then demetaled or neutralized by an inorganic acid to provide an aqueous mixture of L-ascorbic acid and the salt of the inorganic acid, as disclosed in U.S. Pat. No. 2,265,121, the process being hereinafter referred to as the alkyl ester enolizing process.

Various methods are known to remove the inorganic acid or salts of an inorganic acid in the mixture thereof with L-ascorbic acid resulting from the production of L-ascorbic acid as above mentioned. In the direct process, the inorganic acid, e.g., hydrochloric acid, is removed by reacting the acid with a basic compound of lead or silver to form a readily removable water-insoluble compound such as lead chloride or silver chloride, as disclosed in U.S. Pat. No. 2,444,087. As a further method applicable to the direct process for removing the inorganic acid, the acid is neutralized with an alkali such as sodium hydroxide to convert the acid to its alkali salt, such as sodium chloride, and then L-ascorbic acid is separated from the mixture, for example, by crystallization. In the alkyl ester enolizing process, in turn, the metal salt of L-ascorbic acid is reacted with hydrogen chloride gas in an organic solvent such as methanol, to provide L-ascorbic acid and the salt such as sodium chloride, and the latter is separated from L-ascorbic acid. As another method, the metal salt of L-ascorbic acid is demetaled by the use of strongly acidic ion exchange resin.

However, it is very often difficult to remove the inorganic acid used sufficiently from the reaction mixture resulting from the direct process by the prior method as descrived above, thus the prior method fails to provide highly pure L-ascorbic acid. In the case of the alkyl ester enolizing process, when the demetalation of L-ascorbate is carried out in an organic solvent, a much amount of the solvent is needed, whereas when the demetalation is carried out by the use of ion exchange resin, a much amount of an acid is needed to regenerate the ion exchange resin.

On the other hand, a method is already known, as disclosed in Japanese Patent Disclosure No. 47-18858, which separates L-ascorbic acid from a mixture of L-ascorbic acid and carbohydrates such as L-sorbose and L-tagatose by means of electrodialysis. In this method, L-ascorbic acid itself is driven to pass through an anion exchange membrane into a dialysis solution or electrolyte. Therefore, the method may be limited in use to the separation of L-ascorbic acid from its dilute solution of as low as 1% by weight, as described in the prior art, and it may be impractical to adopt the method in order to separate L-ascorbic acid from a mixture of L-ascorbic acid and salts of an inorganic acid.

A further method is also known, as disclosed in Japanese Patent Disclosure No. 50-111062, in which an alkali metal or an alkaline earth metal salt of L-ascorbic acid is first electrodialyzed to demetal the salt in part, and then the remaining salt is demetaled with strongly acidic ion exchange resins. In this method, the demetalation needs two-step operation since, as described in the prior art, the complete electrodialysis is disadvantageous in that it accompanies a great decrease of current efficiency.

The present inventors have made an extensive study to find out an effective method for separating L-ascorbic acid from inorganic acids, as such a mixture results from the direct process, and have found out that a method is very effective which comprises adding an alkali in amounts equivalent to the amount of the inorganic acid in the mixture of L-ascorbic acid and the inorganic acid, to convert the acid to the corresponding salt, and then subjecting the mixture of L-ascorbic acid and the salt to electrodialysis to remove the salt from the mixture. After a further study, the inventors have found out that the electrodialysis is likewise effectively applicable to the purification of L-ascorbic acid by the alkyl ester enolizing process. In the application of the electrodialysis to the reaction mixture by the alkyl ester enolizing process where metal salts of L-ascorbic acid are produced, an inorganic acid is added in amounts equivalent to the amount of the metal salt of L-ascorbic acid in the reaction mixture so as to neutralize the salt to form an aqueous solution of a mixture of L-ascorbic acid and a salt of the inorganic acid, and the the resultant aqueous solution is subjected to the electrodialysis.

An object of this invention is therefore to provide a method of purifying L-ascorbic acid, and in particular, to provide a method of removing salts of an inorganic acid contained in an aqueous solution of L-ascorbic acid.

A method of purifying L-ascorbic acid of the invention comprises: subjecting an acidic aqueous solution of L-ascorbic acid which contains salts of an inorganic acid to electrodialysis to remove the salt therefrom.

The method of the invention is applicable to any acidic aqueous solution of L-ascorbic acid which contains salts of an inorganic acid, and the solution may contain L-ascorbic acid and salts of inorganic acid in any concentration and in any ratio therebetween unless they crystallize out from the solution. However, the method of the invention is advantageously applicable to an acidic aqueous solution which contains L-ascorbic acid in amounts of about 0.1–30% by weight and salts of an inorganic acid in amounts of about 1–25% by weight based on the solution. Either the direct process or the alkyl ester enolizing process provides, as described hereinbefore, such acidic aqueous solutions, and the salt of an inorganic acid in these solutions are therefore those which result from the production of L-ascorbic acid by these processes.

For example, according to the direct process, an aqueous reaction mixture of L-ascorbic acid and an inorganic acid results when heating diacetone-2-keto-L-gulonic acid or 2-keto-L-gulonic acid in the presence of a catalyst of an inorganic acid such as hydrochloric acid. Thus, the addition of an alkali in amounts equivalent to the inorganic acid in the reaction mixture to the reaction mixure forms an acidic aqueous solution of L-ascorbic acid which contains the alkali salt of the inorganic acid such as sodium chloride. In this way, an aqueous solution results which usually contains about 1–5 parts by weight of the alkali salt of inorganic acid in relation to 10 parts by weight of L-ascorbic acid. In the case of the alkyl ester enolizing process, an alkyl ester of 2-keto-L-gulonic acid is enolized and lactonized in a known conventional manner in the presence of a base such as sodium methylate, and the resulting sodium L-ascorbate is neutralized by an equivalent of an inorganic acid such as hydrochloric acid, thereby to provide an acidic aqueous solution of L-ascorbic acid which contains the sodium salt of the acid such as sodium chloride. In this way, an aqueous solution results which usually contains about 3–4 parts by weight of the alkali salt of inorganic acid in relation to 10 parts by weight of L-ascorbic acid. Therefore, the salt of inorganic acid contained in the acidic aqueous solution of L-ascorbic acid resulting from the production of L-ascorbic acid may be sodium chloride, sodium bromide or potassium chloride, and sodium chloride is the commonest in the industrial production of L-ascorbic acid.

Any conventional electrodialysis apparatus is utilizable in the method of the invention. The apparatus in its simplest form is composed of a dialysis compartment, an anode compartment and a cathode compartment both separated from the dialysis compartment by ion exchange membranes on both sides of the dialysis compartment. However, an improved known apparatus is advantageously used in the invention.

The attached drawing is a simplified representation of such an electrodialysis apparatus, which comprises a dialysis compartment 1, and an anode compartment 2 and a cathode compartment 3 on both sides of the dialysis compartment separated therefrom by ion exchange membranes 4 or other diaphragms to prevent the mixing of the entering solutions into the dialysis compartment and electrode compartment. The dialysis compartment has a plurality of anion exchange membranes 5, 5 and a plurality of cation exchange membranes 6, 6 placed alternately so as to form desalting compartments 7 and concentrating compartments 8 alternately. The aqueous solution of L-ascorbic acid which contains salts of an inorganic acid, which is hereinafter referred to as a feed solution, is introduced into the desalting compartment and returned circulatingly to its tank 9 by a pump 10, and a concentrating solution which is usually a saline water, is likewise introduced into the concentrating compartment and returned circulatingly to its tank 11 by a pump 12, while saline water is circulated as electrode solutions between a tank 13 and the respective electrode compartments by a pump 14.

The electrodialysis of the feed solution is carried out in the desalting compartment by applying a voltage across the electrodes, namely the ions forming the salt contained in the feed solution are driven to pass through either of the ion exchange membranes depending upon their electric charges into the concentrating solution, thereby to desalt the feed solution in the desalting compartment.

When desired, the desalting compartment or concentrating compartment is sealed under an inert atmosphere such as nitrogen to prevent air oxidation of L-ascorbic acid.

The aqueous solution thus desalted by the electrodialysis is decolored and purified with activated carbon, concentrated in vacuo so that highly purified L-ascorbic acid crystallizes out.

According to the method of the invention, a selective monovalent anion permeable membrane is preferably used as an anion exchange membrane, although any cation exchange membrane is equally usable. "Selemion ASV" membrane (Asahki Glass K.K.) and "Neosepta ACS" membrane (Tokuyama Soda K.K.) are exemplifications of the selective monovalent anion permeable membrane preferably usable in the invention. An anion exchange membrane for common desalting purpose is also usable in the invention, however, since this common type of membranes is less selectively permeable to monovalent anions, that is, less selectively permeable both to chloride ions and L-ascorbic acid anions, the leakage of L-ascorbic acid to the concentrating solution is greater than in the electrodialysis where the selective monovalent anion permeable membrane is used as anion exchange membranes.

According to the invention, the electrodialysis of acidic aqueous solution containing L-ascorbic acid and salts of inorganic acid is carried out preferably until the desalting rate reaches about 80–99%, although an optimum desalting rate is dependent upon the concentrations of L-ascorbic acid and the salt of inorganic acid in the aqueous solution to be electrodialyzed.

The use of the selective monovalent anion permeable membrane permits the recovery of L-ascorbic acid in recovery rates as high as about 98%. However, when a higher recovery rate is on purpose desired, the concentrating solution resulting from the first electrodialysis is subjected to a second electrodialysis in which the concentrating solution is used as a feed solution. This two times electrodialysis usually enables the recovery of L-ascorbic acid in a recovery rate of more than 99.5%, i.e., an almost quantitative recovery.

The method of the invention is advantageously applicable to the removal of salts of inorganic acid from an aqueous mixture of L-ascorbic acid and salts of an inorganic acid which results from the direct process or the alkyl ester enolizing process for the production of L-ascorbic acid. According to the invention, the salt of an inorganic acid is effectively removed by a single step electrodialysis from the mixture to recover highly purified L-ascorbic acid in high recovery rates at a high current efficiency. As a further advantage of the present invention, the desalted solution contains a reduced amount of water after the electrodialysis on account of electrosmotic water accompanied by the ion transfer, to increase the concentration of L-ascorbic acid in the solution. This is advantageous, for instance, when the desalted solution is concentrated to crystallize out L-ascorbic acid from the solution.

The invention will be understood more readily with reference to the following examples; however, these examples are intended to illustrate the invention only and are not construed as limitation to the invention.

EXAMPLE 1

An electrodialysis apparatus as shown in the drawing with an anode of platinum-plated titanium plate and a cathode of stainless steel (SUS 316) was used which had ten of selective monovalent anion permeable membranes, "Selemion ASV" (Asahi Glass K.K.) as anion exchange membanes, and ten of "Selemion CMV" (Asahi Glass K.K.) as cation exchange membranes placed alternately in the dialysis compartment, each membrane having an effective area of 2 $dm^2$, to form desalting compartments and concentrating compartments alternately.

L-Ascorbic acid was produced by the direct process, and to the resulting aqueous reaction mixture was added sodium hydroxide in amounts equivalent to the amount of hydrochloric acid in the reaction mixture. The resultant aqueous feed solution had a composition of 900 g of L-ascorbic acid and 315 g of sodium chloride (total volume of 4500 ml). Saline solutions were used as a concentrating solution and an electrode solution, respectively. The concentrating solution used was a 0.5%(W/V) aqueous solution of sodium chloride (total volume of 4000 ml) and the electrode solution used was 3.0%(W/V) aqueous solution of sodium chloride.

The feed solution, concentrating solution and electrode solution were pumped from the tanks to the desalting compartment, concentrating compartment and electrode compartment, respectively, at a rate of 4 l per minute at room temperature while applying a constant voltage of 10 V across the electrodes, to carry out the electrodialysis of the feed solution for 4 hours.

The resultant desalted solution was found to contain 886.5 g of L-ascorbic acid and 11.0 g of sodium chloride (total volume of 3800 ml), whereas the concentrating solution was found to contain 324 g of sodium chloride and 13.5 g of L-ascorbic acid, hence the desalting ratio was 96.5% and the current efficiency was 90%, and the leakage ratio of L-ascorbic acid to the concentrating solution was 1.5%.

The desalted solution was concentrated in a conventional manner to crystallize out L-ascorbic acid which was found to contain substantially no sodium chloride.

The above concentrating solution of 4600 ml was subjected to the electrodialysis in the same manner as above for 3 hours, to provide a desalted solution which was found to contain 13.2 g of L-ascorbic acid and 3.0 g of sodium chloride (total volume of 3500 ml) and a concentrating solution containing 0.3 g of L-ascorbic acid (total volume of 4700 ml). Therefore, the desalting ratio was 99%, the current efficiency was 99%, and the leakage of of L-ascorbic acid to the concentrating solution was 2.2%. As a result, the total leakage of L-ascorbic acid through the first and second electrodialysis was 0.033% and the total recovery of L-ascorbic acid was more than 99.9%.

Meanwhile, a further electrodialysis was carried out in the same manner as in the first except that a common desalting membrane, "Selemion AMV" (Asahi Glass K.K.) was used as anion exchange membranes in place of the selective monovalent anion permeable membrane. The leakage of L-ascorbic acid when the desalting ratio reached 96% was 6.5%.

EXAMPLE 2

An electrodialysis apparatus was used which had selective monovalent anion permeable membranes, "Neosepta ACS" (Tokuyama Soda K.K.) and "Neosepa CL-25T" (Tokuyama Soda K.K.) as anion exchange membranes and cation exchange membranes, respectively, provided therewith, and was otherwise the same as in Example 1.

An aqueous solution containing 1750 g of sodium L-ascorbate was obtained by the alkyl ester enolizing process. To this solution was added 922 g of a 35 weight % hydrochloric acid to provide 7000 ml of a feed solution, which was found to contain 1556 g of L-ascorbic acid and 517 g of sodium chloride, and had a pH of 1.9. A 1.0%(W/V) saline solution (total volume of 7000 ml) was used as a concentrating solution and a 3.0%(W/V) saline solution was used as an electrode solution. The feed solution was subjected to the electrodialysis in the same manner as in Example 1 for 5 hours.

The resultant desalted solution was found to contain 1525 g of L-ascorbic acid and 15.5 g of sodium chloride (total volume of 5950 ml), and the concentrating solution was found to contain 31 g of L-ascorbic acid and 571 g of sodium chloride (total volume of 8050 ml). Therefore, the desalting ratio was 97%, the current efficiency was 91%, and the leakage ratio of L-ascorbic acid to the concentrating solution was 2.0%.

What is claimed is:

1. A method of purifying L-ascorbic acid which comprises: subjecting an aqueous solution of L-ascorbic acid which contains alkali salts of an inorganic acid selected from sodium chloride, sodium bromide, and potassium chloride to electrodialysis to remove the salt therefrom.

2. The method as claimed in claim 1 wherein the solution is electrodialyzed by the use of selective monovalent anion permeable membranes as anion exchange membranes.

3. The method as claimed in claim 1 wherein the solution is prepared by heating diacetone-2-keto-L-gulonic acid or 2-keto-L-gulonic acid in the presence of an inorganic acid, and then adding to the resultant reaction mixture an alkali in amounts equivalent to the amount of the inorganic acid in the reaction mixture to convert the inorganic acid to salts of the alkali selected from sodium chloride, sodium bromide, and potassium chloride.

4. The method as claimed in claim 1 wherein the solution is prepared by enolizing and lactonizing an alkyl ester of 2-keto-L-gulonic acid in the presence of an alkali metal base to provide the metal salt of L-ascorbic acid, and then adding to the resulting reaction mixture an inorganic acid in amounts equivalent to the metal salt of L-ascorbic acid in the reaction mixture to provide a mixture of L-ascorbic acid and the metal salts of the inorganic acid selected from sodium chloride, sodium bromide, and potassium chloride.

5. The method of claim 3 wherein the salt of the alkali is sodium chloride.

6. The method of claim 4 wherein the metal salt of the inorganic acid is sodium chloride.

* * * * *